United States Patent [19]

Edwards et al.

[11] Patent Number: 6,001,846
[45] Date of Patent: Dec. 14, 1999

[54] PROCESS FOR THE PREPARATION OF 1,2-DIHYDROQUINOLINES

[75] Inventors: James P. Edwards, San Diego; Todd K. Jones, Solana Beach; Josef D. Riggenberg, San Diego; Erick M. Carreira, Pasadena, all of Calif.

[73] Assignee: Ligand Pharmaceuticals Incorporated, San Diego, Calif.

[21] Appl. No.: 09/024,986

[22] Filed: Feb. 17, 1998

[51] Int. Cl.⁶ .......................... A61K 31/47; C07D 471/02
[52] U.S. Cl. ........................ 514/285; 546/62; 546/77; 546/78
[58] Field of Search ........................ 514/285; 546/62, 546/77, 78

[56] References Cited

U.S. PATENT DOCUMENTS

| 5,688,808 | 11/1997 | Jones et al. | 514/285 |
| 5,688,810 | 11/1997 | Jones et al. | 514/311 |
| 5,693,646 | 12/1997 | Jones et al. | 514/285 |
| 5,693,647 | 12/1997 | Jones et al. | 514/285 |
| 5,696,127 | 12/1997 | Jones et al. | 514/285 |
| 5,696,130 | 12/1997 | Jones et al. | 514/291 |
| 5,696,133 | 12/1997 | Jones et al. | 514/314 |

FOREIGN PATENT DOCUMENTS 9619458  6/1996  WIPO .

OTHER PUBLICATIONS

R. H. F. Manske and M. Kulka, *Organic Reactions*, 7(1953) 59–98.

W. R. Vaughan, *Org. Synth. Coll.* vol. III (1955) 329–332.

D. W. Knight, In *Comprehensive Organic Synthesis: Selectivity, Strategy & Efficiency in Modern Organic Chemisty* vol. 3, B. M. Trost (Ed.), Pergamon: New York (1991) 481–520.

T. N. Mitchell, *Synthesis* (1992) 803–815.

M. E. Krolski, A. F. Renaldo, D. E. Rudisill and J. K. Stille, *J. Org. Chem.*, 53 (1988) 1170–1176.

I. P. Beletskaya, J. Organomet. Chem., 250 (1983) 551–564.

N. Miyaura, T. Yanagi and A. Suzuki, *Synth. Commun.*, 11 (1981) 513–519.

A. Suzuki, *Pure Appl. Chem.*, 63 (1991) 419–422.

H. Walter, *Helv. Chim. Acta*, 75 (1992) 1274–1280.

H. Walter and J. Schneider, *Heterocycles*, 41 (1995) 1251–1269.

*Primary Examiner*—John Kight
*Assistant Examiner*—Charanjit S. Aulakh
*Attorney, Agent, or Firm*—James Scott Elmer; William L. Respess

[57] ABSTRACT

A method for preparing 1,2-dihydroquinolines that is more flexible than the Skraup reaction is provided. The method comprises treating an ortho-alkenyl aniline with a ketone in the presence of a Lewis acid. Novel intermediates and products of this method useful as steroid receptor modulators, as well as pharmaceutical compositions and methods of use thereof are also claimed.

53 Claims, No Drawings

PROCESS FOR THE PREPARATION OF 1,2-DIHYDROQUINOLINES

FIELD OF THE INVENTION

This invention relates to 1,2-dihydroquinoline compounds that are useful as steroid receptor modulators and as key intermediates in the preparation of steroid receptor modulators, and methods for their synthesis.

Pat. No. 5,696,127}, and are prepared by a multi-step route culminating in the treatment of an aniline of structure 5 with a ketone and iodine at elevated temperatures in a process known as the Skraup reaction {see: "The Skraup Synthesis of Quinolines", R. H. F. Manske and M. Kulka, *Organic Reactions*, 7 (1953) 59–98; "2,4-Dimethylquinoline", W. R. Vaughan, *Org. Synth. Coll. Vol III*, (1955) 329–332}:

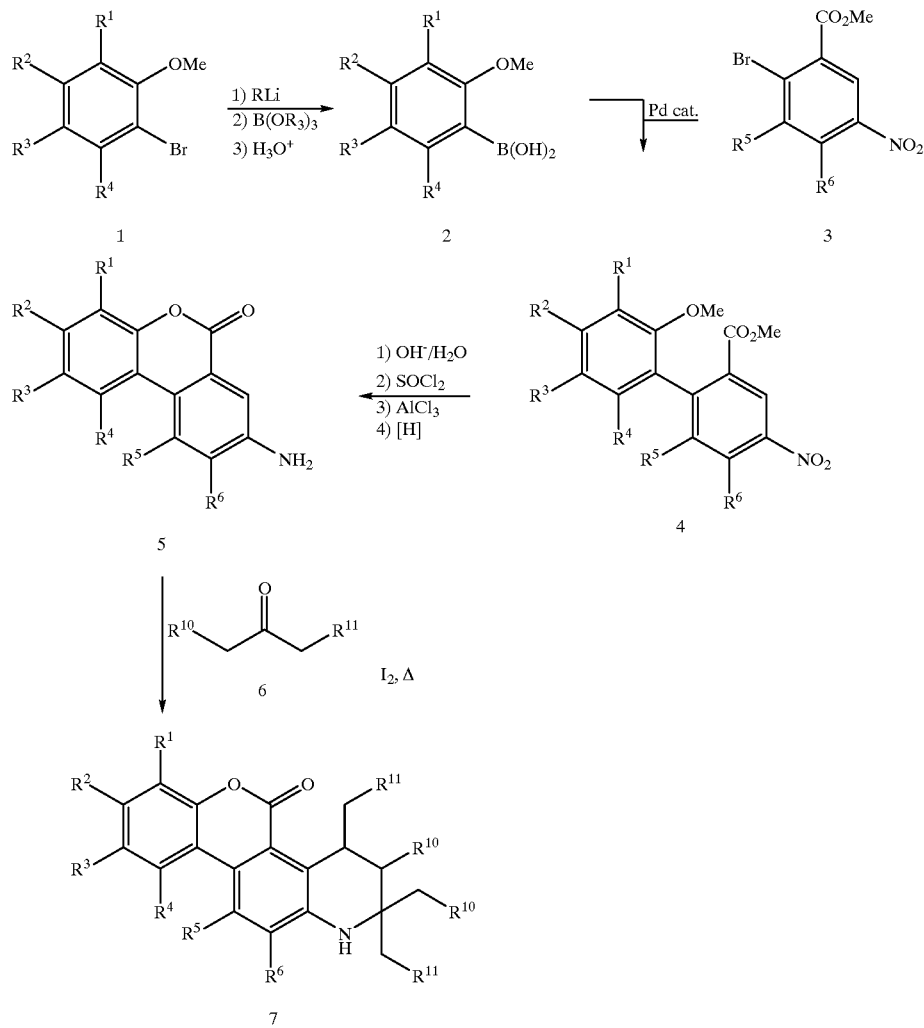

BACKGROUND OF THE INVENTION

Tetracyclic 1,2-dihydroquinolines of structure 7 are key intermediates in the preparation of a number of steroid receptor modulating compounds {see for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, C. M. Tegley, L. Zhi, J. P. Edwards, S. J. West, U.S. Pat. No. 5,693,646; "Steroid Receptor Modulator Compounds and Methods", T. K. Jones, L. Zhi, J. P. Edwards, C. M. Tegley, S. J. West, U.S.

Many 1,2-dihydroquinolines of structure 7 are themselves steroid receptor modulating compounds. {See for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, C. M. Tegley, D. T. Winn, L. G. Hamann, J. P. Edwards, S. J. West, U.S. Pat. No. 5,693,647.} Other 2,2-disubstituted 1,2-dihydroquinolines are also modulators of steroid receptors. {See for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, D. T. Winn, L. Zhi, L. G. Hamann, C. M. Tegley, C. L. F. Pooley, U.S. Pat. No. 5,688,808; "Steroid Receptor Modulator Compounds and Methods", T. K. Jones, M. E. Goldman, C. L. F. Pooley, D. T. Winn, J. P. Edwards, S. J. West, C. M. Tegley, L. Zhi, U.S. Pat. No. 5,688,810; "Steroid Receptor Modulator Compounds and Methods", T. K. Jones, D. T. Winn, M. E. Goldman, L. G. Hamann, L. Zhi, L. J. Farmer, R. L. Davis, U.S. Pat. No. 5,696,130; "Steroid Receptor Modulator Compounds and Methods", T. K. Jones, M. E. Goldman, C. L. F. Pooley, D. T. Winn, J. P. Edwards, S. J. West, C. M. Tegley, L. Zhi, L. G. Hamann, L. J. Farmer, R. L. Davis, U.S. Pat. No. 5,696,133.}

The conversion of 5 to 7 utilizing a Skraup reaction limits the variety of compounds that can be prepared by this route due to the need to use a ketone (6) as one of the reaction partners; the substituents on C(2)–C(4) cannot be varied independently. The present invention addresses this limiting aspect of the Skraup reaction.

SUMMARY OF THE INVENTION

The present invention provides a novel route for the conversion of anilines 5 to 1,2-dihydroquinolines 12 (the set of compounds represented by general structure 7 being recognized as a subset of the set of compounds represented by general structure 12) in which the substituents on C(2)–C(4) can be varied independently:

(Ed.), Pergamon: N.Y., (1991) 521–550; "Palladium-Catalysed Reactions of Organotin Compounds", T. N. Mitchell, *Synthesis*, (1992) 803–815; "Palladium-Catalyzed Coupling of 2-Bromoanilines with Vinylstannanes—A Regiocontrolled Synthesis of Substituted Indoles", M. E. Krolski, A. F. Renaldo, D. E. Rudisill and J. K. Stille, *J. Org. Chem.*, 53 (1988) 1170–1176; "The Cross-Coupling Reactions of Organic Halides with Organic Derivatives of Tin, Mercury, and Copper Catalyzed by Palladium", I. P. Beletskaya, *J. Organomet. Chem.*, 250 (1983) 551–564; "The Palladium-Catalyzed Cross-Coupling Reaction of Phenylboronic Acid with Haloarenes in the Presence of Bases", N. Miyaura, T. Yanagi and A. Suzuki, *Synth. Commun.*, 11 (1981) 513–519; "Synthetic Studies via the Cross-coupling Reaction of Organoboron Derivatives with Organic Halides", A. Suzuki., *Pure Appl. Chem.*, 63 (1991) 419–422. } An ortho-alkenyl aniline 10 can be converted to the target compounds 12 by reaction with a ketone 11 and an appropriate catalyst. {See for example: "Eine Neue Einfache Synthese Spirocyclischer 1H-Chinolin-Derivatives", H. Walter, *Helv. Chim. Acta*, 75 (1992) 1274–1280; "Acid Catalyzed Reactions of 2-Vinylaniline Derivatives with Cylic Ketones of the Tetralone-, Chroman-4-one- and 2,3-Dihydro-1H-Quinolin-4-ones Series. N(O)-Heterocycles via 6π Electronic Rearrangements or [1,5] Dipolar Electrocyclizations. Part 3", H. Walter and J. Schneider, *Heterocycles*,

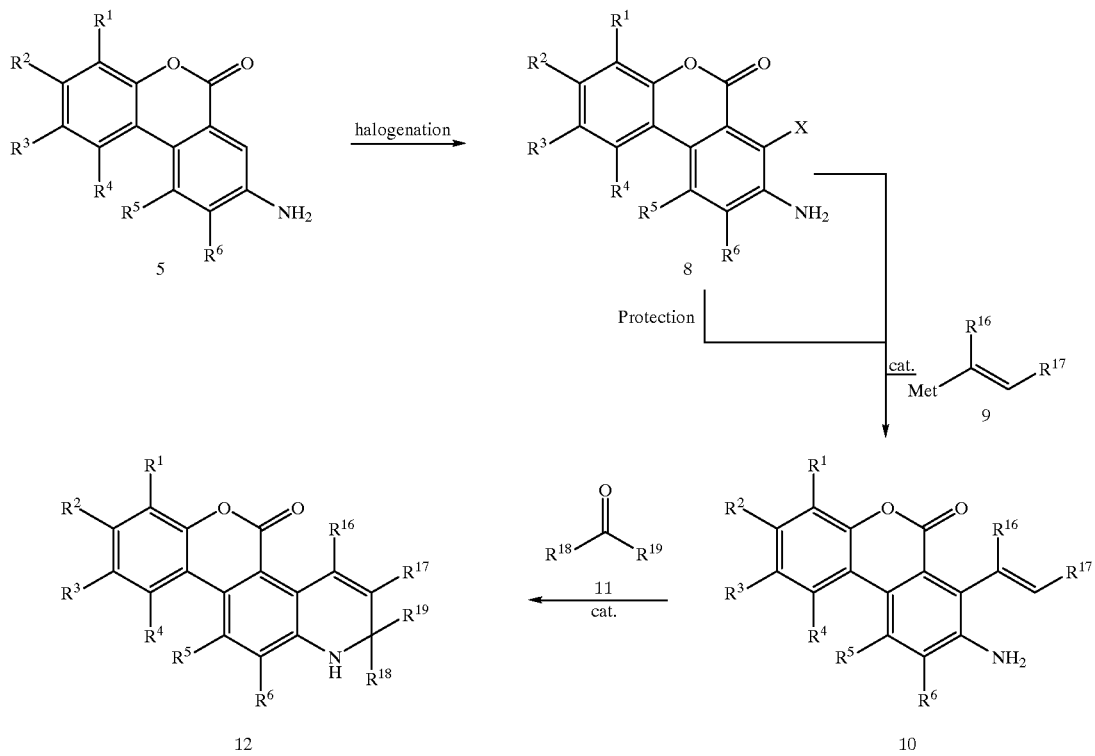

First the carbon atom flanked by the aniline nitrogen and lactone carbonyl is functionalized with a halogen atom, forming a compound of structure 8. Performing a cross-coupling reaction of 8 (or an N-protected analogue of 8) with an appropriately substituted metalated olefin 9 affords an ortho-alkenyl aniline 10, by a process known as a Stille, Suzuki, or Negishi coupling. {See for example: "Coupling Reactions Between sp² Carbon Centers", D. W. Knight, In *Comprehensive Organic Synthesis: Selectivity, Strategy & Efficiency in Modern Organic Chemistry* Vol. 3, B. M. Trost 41 (1995) 1251–1269.}. Using this alternative procedure, compounds with substitution patterns not available from the traditional Skraup reaction route are now readily accessible.

The present invention is directed to methods for the preparation of 1,2-dihydroquinolines, some of which are key intermediates in the preparation of steroid receptor modulating compounds and/or are themselves steroid receptor modulators. The invention provides a novel route to compounds of structure 12 and, more particularly, to 1,2- dihydroquinolines that are not accessible from a previously disclosed route. Intermediate compounds prepared enroute to 1,2-dihydroquinolines of structure 12 as well as compounds of structure 12 that cannot be synthesized via the traditional Skraup reaction (i.e. the reaction that yields 7 directly from 5) are also within the scope of this invention. In addition, the general process consisting of the preparation of 2,2-disubstituted 1,2-dihydroquinolines optionally substituted at C(3) and/or C(4) by treatment of an ortho-alkenyl aniline with a ketone in the presence of a Lewis acid is also within the scope of this invention.

DEFINITIONS

In accordance with the present invention and as used herein, the following terms are defined with the following meanings, unless explicitly stated otherwise.

The terms "alkyl" and "allyl" refer to straight-chain, branched-chain, and cyclic structures, and combinations thereof. These "alkyl" and "allyl" structures may be optionally substituted with one or more heteroatoms, including for example, without limitation, fluorine, oxygen, nitrogen, phosphorus and sulfur.

The term "aryl" refers to an optionally substituted, six-membered aromatic ring, including polyaromatic rings.

The term "heteroaryl" refers to an optionally substituted, five-membered heterocyclic ring containing one or more heteroatoms selected from the group consisting of carbon, oxygen, nitrogen and sulfur, including polycyclic rings or six-membered heterocyclic rings containing one or more heteroatoms selected from the group consisting of carbon and nitrogen, including polycyclic rings.

A 1,2-dihydroquinoline is defined by the following structure:

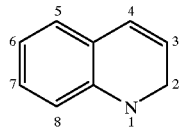

A 1,2-dihydro-5-coumarino[3,4-f]quinoline is defined by the following structure:

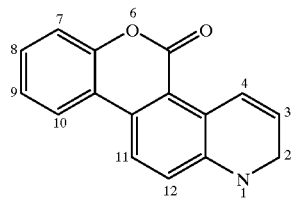

DETAILED DESCRIPTION OF THE INVENTION

The novel process for the preparation of a 1,2-dihydroquinoline of structure 12 comprises a multi-step process initiated by treating an aniline 5, the preparation of which has been previously disclosed {see for example: "Preparation of Quinolines and Fused Quinolines as Steroid Receptor Modulators", T. K Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, C. M. Tegley, D. T. Winn, L. G. Hamann, J. P. Edwards, S. J. West, U.S. Pat. No. 5,693,647}, with a halogenating agent, especially bromine or N-bromosuccinimide:

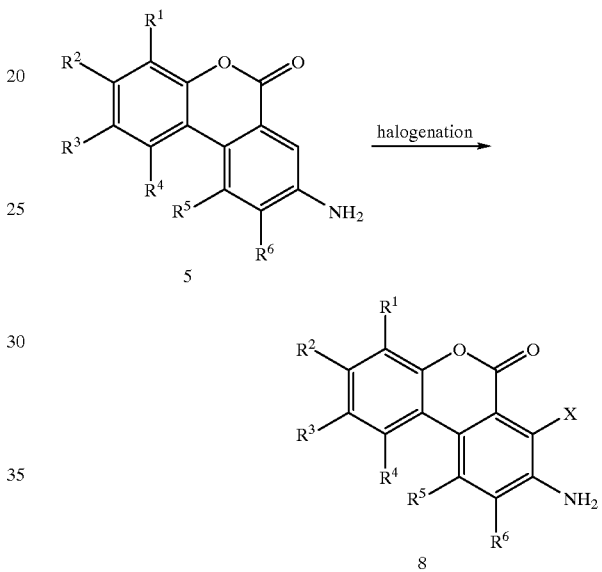

wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$; and X represents chloro, bromo, or iodo.

In an optional second step, the nitrogen atom of the ortho-haloaniline may be protected, especially as an N-trimethylsilyl or as an N-trifluoroacetyl analogue:

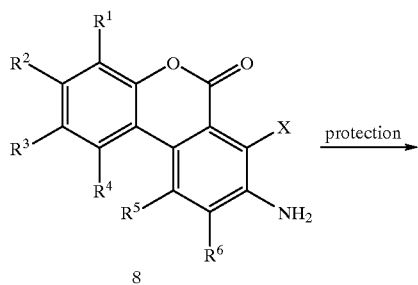

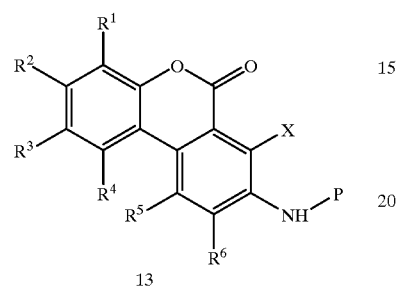

1-methoxy-1-ethenylboronic acid, in the presence of a catalyst or catalysts, especially tetrakis(triphenylphosphine) palladium (0) or palladium acetate/tri(2-furyl)phosphine/copper(I) iodide, to afford an ortho-alkenylaniline. In the case of 8, the cross-coupling product 10 is obtained directly. In the case of 13, the cross-coupling product 10 is obtained after a de-protection step:

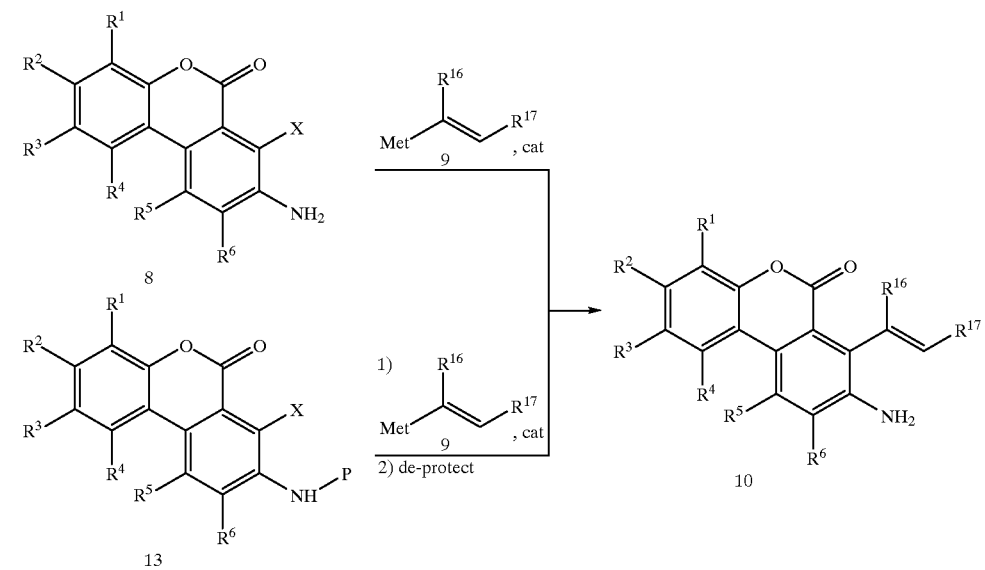

wherein P represents $SiR^{10}R^{11}R^{12}$ (where $R^{10-12}$ independently represent $C_1$–$C_6$ alkyl, substituted $C_1$–$C_6$ alkyl, allyl, substituted allyl, aryl, substituted aryl, heteroaryl or substituted heteroaryl); $COR^{13}$ (where $R^{13}$ represents $CF_3$, $C_1$–$C_6$ alkyl, substituted $C_1$–$C_6$ alkyl, aryl or substituted aryl); $CO_2R^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl); $CONR^{14}R^{15}$ (where $R^{15}$ represents H, $C_1$–$C_6$ alkyl, substituted $C_1$–$C_6$ alkyl, allyl, substituted allyl, aryl, substituted aryl, heteroaryl or substituted heteroaryl; or where $R^{14}$ and $R^{15}$ taken together form a five- to seven-membered ring); benzyl or substituted benzyl; or allyl or substituted allyl.

In a subsequent step, an ortho-haloaniline 8 or N-protected ortho-haloaniline 13 is treated with a metallated olefin 9, especially 2-(tributylstannyl)propene or wherein $R^{16-17}$ independently represent H, $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a five- to seven-membered, optionally substituted ring. It will be recognized by those skilled in the art that the geometry of 9 can be either E or Z or a mixture of both, affording compounds 10 as either E or Z isomers, or a mixture of both.

In the final step of this novel process, an aniline 10 is treated with a ketone 11, especially acetone, cyclohexanone or 3-pentanone, in the presence of a catalyst, especially camphor sulfonic acid, boron trifluoride etherate or lanthanum tris(trifluoromethanesulfonate), to afford the 1,2-dihydroquinoline 12:

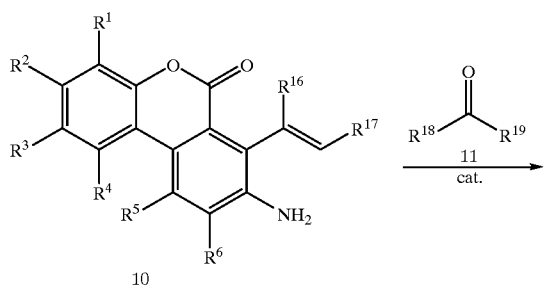

10

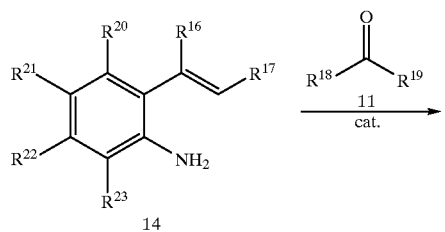

12 wherein $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered (preferably five- to eight-membered), optionally substituted ring.

In a more general sense, an optionally substituted aniline (with hydrogen at an ortho position) can be halogenated to form an ortho-haloaniline that is subsequently treated with a metallated olefin in the presence of a catalyst or catalysts to form an ortho-alkenyl aniline of structure 14 (wherein: $R^{16}$ and $R^{17}$ have the definitions detailed above; and $R^{20-23}$ independently represent H, $C_1$–$C_6$ alkyl, substituted $C_1$–$C_6$ alkyl, F, Cl, Br, I, CN, $CF_3$, $CF_2CF_3$, $CO_2R^7$, $CONR^7R^8$ (where $R^7$ and $R^8$ have the definitions detailed above), allyl, substituted allyl, aryl, substituted aryl, heteroaryl or substituted heteroaryl; or where $R^{20}$ and $R^{21}$ OR $R^{21}$ and $R^{22}$ OR $R^{22}$ and $R^{23}$ taken together form a five- to seven-membered ring). The ortho-alkenyl aniline of structure 14 may be converted to an optionally substituted 2,2-disubstituted 1,2-dihydroquinoline by treatment of 14 with a ketone 11 (wherein $R^{18}$ and $R^{19}$ have the definitions detailed above, especially acetone, cyclohexanone, 3-pentanone or an optionally substituted acetophenone) and a Lewis acid (especially boron trifluoride etherate, lanthanum tris (trifluoromethanesulfonate) or chlorotitanium triisopropoxide) to afford the 1,2-dihydroquinoline 15.

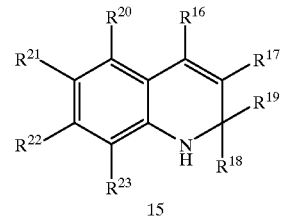

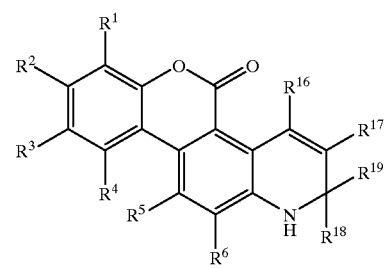

The nitrogen atom of the ortho-haloaniline may be protected prior to treatment with a metallated olefin, in which case the cross-coupling product 14 is obtained after a de-protection step.

The 1,2-dihydroquinolines 12 are useful for the preparation of steroid receptor modulating compounds that have a variety of therapeutic applications, depending upon their specific biological activity. {See for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, C. M. Tegley, L. Zhi, J. P. Edwards, S. J. West, U. S. Pat. No. 5,693,646; "Steroid Receptor Modulator Compounds and Methods", T. K. Jones, L. Zhi, J. P. Edwards, C. M. Tegley, S. J. West, U.S. Pat. No. 5,696,127}. Many 1,2-dihydroquinolines of structure 7, a subset of the compounds represented by structure 12, are themselves steroid receptor modulating compounds. In particular, several compounds of structure 7 are known to be progesterone receptor (PR) modulators (i.e., PR agonists, partial agonists, and antagonists). {See for example: "Steroid Receptor Modulator Compounds and Methods", T. K. Jones, L. Zhi, C. M. Tegley, D. T. Winn, L. G. Hamann, J. P. Edwards, S. J. West, U.S. Pat. No. 5,693,647.}

Compounds of the present invention, the synthesis of which is made possible by the methods taught herein, are defined as those having the structural formula:

12 wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$;

$R^{16}$ represents H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; $R^{17}$ represents $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered (preferably five- to eight-membered), optionally substituted ring.

The compounds of the present invention also include racemates, stereoisomers and mixtures of said compounds. Such isomers can be isolated by standard resolution techniques, including fractional crystallization and chiral column chromatography.

Preferably, structure 12 compounds of the present invention, defined immediately above, comprise steroid receptor modulators. More preferably, structure 12 compounds of the present invention comprise progesterone receptor (PR) modulators (agonists, partial agonists and antagonists).

In a further preferred aspect, the present invention comprises a method of modulating processes mediated by steroid receptors comprising administering to a patient an effective amount of a compound of the structure 12, wherein $R^1$ through $R^{19}$ have the definitions given above for compounds of the present invention.

The progesterone receptor (PR) modulator compounds of the present invention are particularly useful for hormone replacement therapy and as modulators of fertility (e.g., as contraceptives, contragestational agents or abortifacients), either alone or in conjunction with estrogen receptor (ER) modulators. The PR active compounds are also useful in pregnancy maintenance therapy; the treatment of dysfunctional uterine bleeding, dysmenorrhea, endometriosis, leiomyomas (uterine fibroids), mood disorders and cardiovascular disease; treating tumors of the central nervous system, such as meningiomas; as well as treating various hormone-dependent cancers, including, without limitation, cancers of the breast, ovaries, endometrium and prostate. {See for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, C. M. Tegley, D. T. Winn, L. G. Hamann, J. P. Edwards, S. J. West, U.S. Pat. No. 5,693,647.}

It will be understood by those skilled in the art that, while the compounds of the present invention will typically be employed as selective agonists, partial agonists or antagonists, there may be instances where a compound with a mixed steroid receptor profile is preferred, including, without limitation, mixed PR/AR, PR/MR or PR/GR modulators. For example, use of a PR agonist (i.e., progestin) in female contraception often leads to the undesired effects of increased water retention and acne flare-ups. In this instance, a compound that is primarily a PR agonist, but also displays some androgen receptor (AR) and mineralocorticoid receptor (MR) antagonist activity, may prove useful. Specifically, the mixed MR effects would be useful to control water balance in the body, while the AR effects would help to control any acne flare-ups that occur.

The present invention also provides a pharmaceutical composition comprising an effective amount of a steroid receptor-modulating structure 12 compound of the present invention, or a pharmaceutically acceptable salt thereof, and a pharmaceutically acceptable carrier.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenilacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino and tris(hydoxymethyl) aminomethane. Additional pharmaceutically acceptable salts are known to those skilled in the art.

As noted above, any of the steroid receptor-modulating compounds of the present invention, or the pharmaceutically acceptable salts thereof, can be combined in a mixture with a pharmaceutically acceptable carrier to provide compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the pharmaceutical compositions or compounds in oral liquid dosage forms (e.g., suspensions, elixirs and solutions), typical pharmaceutical media such as water, glycols, oils, alcohols, flavoring agents, preservatives, coloring agents and the like can be employed. Similarly when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions or compounds of the present invention.

For parenteral administration the carrier will typically comprise sterile water, although other ingredients that aid in solubility or serve as preservatives may also be included. Furthermore, injectable suspensions may also be prepared, in which case appropriate liquid carriers, suspending agents and the like will be employed.

For topical administration, the pharmaceutical compositions and compounds of the present invention may be formulated using bland, moisturizing bases, such as ointments or creams. Examples of suitable ointment bases are petrolatum, petrolatum plus volatile silicones, lanolin, and water-in-oil emulsions such as Eucerin™ (Beiersdorf). Examples of suitable cream bases are Nivea™ Cream (Beiersdorf), cold cream (USP), Purpose Cream™ (Johnson & Johnson) hydrophilic ointment (USP), and Lubriderm™ (Warner-Lambert).

The pharmaceutical compositions and compounds of the present invention will generally be administered in the form of a dosage unit (e.g., tablet, capsule etc.) from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition administered to a patient, according to the present invention, will depend upon a number of factors, including, without limitation, the biological activity desired, the condition of the patient, and tolerance for the drug.

The pharmaceutical compositions and compounds of the present invention can advantageously be used in the treatment of the diseases and conditions described herein. In this regard, the compositions and compounds of the present invention will prove particularly useful in hormone replacement therapy and modulating fertility, either alone or in conjunction with estrogen receptor (ER) modulators. The PR active compounds are also useful in pregnancy maintenance therapy; the treatment of dysfunctional uterine bleeding, dysmenorrhea, endometriosis, leiomyomas, mood disorders and cardiovascular disease; treating tumors of the central nervous system; and treating hormone-dependent cancers, such as cancers of the breast, ovaries, endometrium and prostate.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

The compounds of this invention also have utility when radio- or isotopically-labeled as ligands for use in assays to determine the presence of steroid receptors in a cell background or extract. They are particularly useful due to their ability to selectively activate progesterone receptors (PR), and can therefore be used to determine the presence of such receptors in the presence of other steroid receptors or related intracellular receptors.

Due to the selective specificity of many of the compounds of this invention for PR, these compounds can be used to purify samples of PR in vitro. Such purification can be carried out by mixing samples containing steroid receptors with one or more of the compounds of the present invention so that the compounds bind to the receptor of choice, and then separating out the bound ligand/receptor combination by separation techniques that are known to those of skill in the art. These techniques include column separation, filtration, centrifugation, tagging and physical separation, and antibody complexing, among others.

In yet another aspect, the present invention provides novel intermediates useful in the preparation of the steroid modulator compounds of structure 12. The intermediates of the present invention are defined as those having the structural formulas:

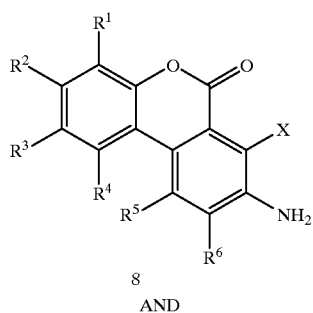

8
AND

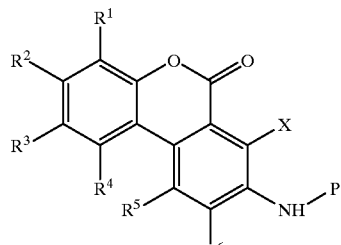

13
AND

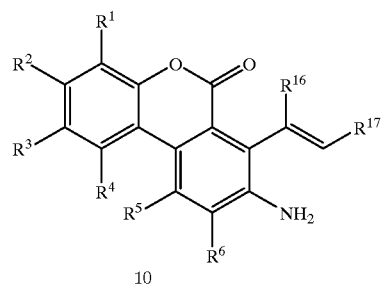

10 wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$;

X represents chloro, bromo, or iodo;

P represents $SiR^{10}R^{11}R^{12}$ (where $R^{10-12}$ independently represent $C_1$–$C_6$ alkyl, substituted $C_1$–$C_6$ alkyl, allyl, substituted allyl, aryl, substituted aryl, heteroaryl or substituted heteroaryl); $COR^{13}$ (where $R^{13}$ represents $CF_3$, $C_1$–$C_6$ alkyl, substituted $C_1$–$C_6$ alkyl, aryl or substituted aryl); $CO_2R^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl); $CONR^{14}R^{15}$ (where $R^{15}$ represents H, $C_1$–$C_6$ alkyl, substituted $C_1$–$C_6$ alkyl, allyl, substituted allyl, aryl, substituted aryl, heteroaryl or substituted heteroaryl; or where $R^{14}$ and $R^{15}$ taken together form a five- to seven-membered ring); benzyl or substituted benzyl; or allyl or substituted allyl;

and $R^{16-17}$ independently represent H, $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a five- to seven-membered, optionally substituted ring.

The intermediates of the present invention also include racemates, stereoisomers and mixtures of said compounds. Such isomers can be isolated by standard resolution techniques, including fractional crystallization and chiral column chromatography.

All cited publications are incorporated by reference herein. All the compounds disclosed in the cited publications are incorporated by reference herein, including those compounds disclosed and referred to in articles cited by the publications mentioned herein.

EXAMPLES

Example 1

Step A

2-Amino-1-bromo-6-fluoro-3,4-benzocoumarin (compound 16, structure 8 where $R^{1-2}=R^{4-6}=H$; $R^3$=fluoro; X=bromo). In a 200-mL r.b. flask, a suspension of 2-amino-6-fluoro-3,4-benzocoumarin (0.89 g, 3.9 mmol) in acetonitrile (40 mL) was cooled to 0° C., and a solution of bromine (620 mg, 3.9 mmol, 1.0 equiv) in $CH_2Cl_2$ (5 mL) was added dropwise over a 5 min period. The reaction mixture was stirred for 10 min at 0° C. and allowed to warm to rt. The reaction mixture was treated with 2% NaOH (100 mL). The resulting orange solid was collected by filtration, washed with hexane (100 mL), and dried in vacuo to afford 0.72 g (60%) of 16 as an orange solid. Data for 16: $^1$H NMR (400 MHz, acetone-$d_6$) 8.16 (d, J=8.7, 1H), 7.89 (dd, J=10.0, 2.9, 1H), 7.47 (d, J=8.7, 1H), 7.32 (dd, J=9.1, 4.9, 1H), 7.12 (td, J=8.0, 3.0, 1H), 5.86 (br exch s, 2H); $^{13}$C NMR (DMSO-$d_6$): 158.7 (d, $J_{C-F}$=239), 157.4, 148.8, 145.5, 124.5, 123.2, 121.5, 119.7 (d, $J_{C-F}$=9), 119.3, 118.1 (d, $J_{C-F}$=9), 115.5 (d, $J_{C-F}$=25), 108.5 (d, $J_{C-F}$=25), 105.9.

Step B

2-Amino-6-fluoro-1-(2-propenyl)- 3,4-benzocoumarin (compound 17, structure 10 where $R^{1\text{-}2}=R^{4\text{-}6}=R^{17}=H$; $R^3$=fluoro; $R^{16}$=methyl). In a 20-mL r.b. flask, a solution of 16 (92 mg, 0.30 mmol) in N-methylpyrrolidone (3 mL) was treated with N,O-bis(trimethylsilyl)acetamide (80 μL, 0.32 mmol, 1.1 equiv) and stirred at rt for 2 h. Tris (dibenzylideneacetone)dipalladium (9.2 mg, 0.010 mmol, 3.3 mol %), tri(2-furyl)phosphine (10.2 mg, 0.0439 mmol, 14.7 mol %), copper(I) iodide (20.1 mg, 0.106 mmol, 35.4 mol %), and 2-(tributylstannyl)propene (0.11 g, 0.33 mmol, 1.1 equiv) were added, and the reaction mixture heated to 80° C. for 6 h. The reaction mixture was allowed to cool to rt and treated with 1 M KF for 1 h, poured into saturated $NH_4Cl$ (5 mL), and extracted with EtOAc (3×4 mL). The extracts were washed with brine (1×5 mL), combined, dried (MgSO4), filtered, and concentrated. Purification by silica gel chromatography (hexane/EtOAc, 2:1) afforded 20 mg (25%) of 17 as an orange solid. Data for 17: $^1$H NMR (400 MHz, acetone-$d_6$) 8.06 (d, J=8.7, 1H), 7.87 (dd, J=10.1, 2.9, 1H), 7.37 (d, J=8.7, 1H), 7.28 (dd, J=9.0, 4.9, 1H), 7.16 (td, J=8.1, 2.9, 1H), 5.30 (q, J=1.5, 1H), 5.20 (exch s, 1H), 4.82 (q, J=1.2, 1H), 2.08 (s, 3H); $^{13}$C NMR (acetone-$d_6$): 160.2 (d $J^{C-F}$=239), 159.3, 147.7, 147.3, 144.4, 129.9, 124.6 (d, $J_{C-F}$=2), 123.5, 122.6, 121.5 (d, $J_{C-F}$=9), 120.1, 119.1 (d, $J_{C-F}$=9), 115.8 (d, $J_{C-F}$=25), 114.6, 108.8 (d, $J_{C-F}$=25), 23.1.

Step C

9-Fluoro-1,2-dihydro-2,2,4-trimethyl-5-coumarino[3,4-f] quinoline (compound 18, structure 12, where $R^{1\text{-}2}=R^{4\text{-}6}=R^{17}=H$; $R^3$=fluoro; $R^{16}=R^{18\text{-}19}$=methyl). In a 20-mL resealable pressure tube, a solution of 17 (25 mg) was dissolved in toluene (2 mL) and treated with acetone (0.5 mL) and camphor sulfonic acid (2 mg). The pressure tube was sealed and heated to 115° C. for 10 h. The reaction mixture was cooled to rt, poured into $H_2O$ (5 mL), and extracted with EtOAc (3×6 mL). The extracts were washed with brine (1×5 mL), combined, dried (MgSO$_4$), filtered, and concentrated to afforded an orange solid. Purification by silica gel chromatography ($CH_2Cl_2$/hexanes, 1:1 to 1.5:1 gradient) afforded 15 mg (50%) of compound 18 as a bright yellow solid. Data for Compound 18: $^1$H NMR (acetone-$d_6$): 7.95 (d, J=8.7, 1 H); 7.83 (dd, J=10.1, 2.9, 1 H); 7.29 (dd, J=9.0, 4.9, 1 H); 7.22 (d, J=8.7, 1 H); 7.17 (m, 1 H); 6.25 br s, 1 H); 5.54 (t, J=1.2, 1 H); 2.06 (s, 3H), 1.30 (s, 6 H); $^{13}$C NMR (acetone-$d_6$): 160.2 (d, $J_{C-F}$=239), 159.9, 148.2, 147.3, 132.9, 131.7, 125.3, 123.0, 121.9, 121.8, 119.1, 118.9 (d, $J_{C-F}$=9.0), 115.6 (d, $J_{C-F}$=25), 108.9 (d, $J_{C-F}$=26), 51.0, 28.5, 21.6.

Example 2

Step A

2-Amino-1-bromo-6-fluoro-3,4-benzocoumarin (compound 16, structure 8 where $R^{1\text{-}2}=R^{4\text{-}6}=H$; $R^3$=fluoro; X=bromo). In an oven-dried 250-mL flask was weighed out 2-amino-6-fluoro-3,4-benzocoumarin (2.58 g, 11.3 mmol). The flask was evacuated and the atmosphere replaced with nitrogen. Anhydrous DMF was added (100 mL), and to the resulting solution was added dropwise a solution of N-bromosuccinimide (2.00 g, 11.3 mmol, 1.00 equiv) in anhydrous DMF (50 mL) over a period of 25 min. The reaction was monitored by TLC and appeared complete after 15 min. After stirring the reaction mixture an additional 45 min at rt, $H_2O$ (100 mL) was added. The reaction mixture was filtered on a Büchner funnel, and the filter cake and paper were added to boiling EtOH/$CH_3CN$ (4:1, 500 mL). The resulting suspension was filtered hot, and recrystallization from this solution afforded 1.84 g (53%) of 16 as copper-colored needles. An additional 0.99 g (29%) of 16 was obtained from the concentrated mother liquors. The $^1$H and $^{13}$C NMR spectra of both samples were identical to those of material prepared above.

Step B

1-Bromo-6-fluoro-2-trifluoroacetamido-3,4-benzocoumarin (compound 19, structure 13 where $R^{1\text{-}2}=R^{4\text{-}6}=H$; $R^3$=fluoro; P=trifluoroacetyl; X=bromo). To a suspension of 16 (1.00 g, 3.25 mmol) in $CH_2Cl_2$ (100 mL) at rt was added $Et_3N$ (1.4 mL, 9.4 mmol, 3.0 equiv). Trifluoroacetic anhydride (1.15 mL, 8.13 mmol, 2.50 eq) was added dropwise and the reaction mixture was stirred for 15 min. The reaction mixture was poured into $H_2O$/brine (1:1, 200 mL) and the crude product extracted with $CH_2Cl_2$ (2×100 mL). The combined organic extracts were washed with $H_2O$/brine (1:1, 100 mL), dried ($Na_2SO_4$), filtered, and concentrated to afford 1.31 g (quant) of 19 as a light brown solid. Data for 19: $^1$H NMR (400 MHz, benzene-$d_6$): 8.63 (br s, 1H); 8.35 (d, J=9.0, 1H); 7.00 (dd, J=9.2, 2.9, 1H); 6.87 (d, J=9.0, 1H); 6.66 (dd, J=8.9, 4.7, 1H); 6.56 (td, J=8.3, 2.1, 1H)

Step C

2-Amino-6-fluoro-1-(2-propenyl)-3,4-benzocoumarin (compound 17, structure 10 where $R^{1\text{-}2}=R^{4\text{-}6}=R^{17}=H$; $R^3$=fluoro; $R^{16}$=methyl). In an oven-dried 100-mL 3-neck flask, a solution of 19 (500 mg, 1.24 mmol), tri(2-furyl)phosphine (58 mg, 0.25 mmol, 20 mol %), and 2-(tributylstannyl)propene (0.422 mL, 1.36 mmol, 1.10 equiv) in dioxane (40 mL) was degassed by freeze/pump/thaw three times. Bis(benzonitrile)dichloropalladium(II) (48 mg, 0.12 mmol, 10 mol %) was added under positive pressure of $N_2$, and the reaction mixture was heated to reflux for 13.5 h. The reaction mixture was poured into acetonitrile (50 mL), and the acetonitrile layer was washed with hexanes (3×50 mL). The hexane layer was extracted with acetonitrile (1×20 mL), and the combined acetonitrile extracts were filtered and concentrated to afford 750 mg of a brown semi-solid. This material was suspended in 95:5 EtOH:$H_2O$ (20 mL) and heated to reflux for 16 h. Only partial conversion was indicated by TLC, so sodium bicarbonate (416 mg, 4.96 mmol, 4.0 equiv) was added and the reaction mixture was heated at reflux until TLC showed full conversion (6.5 h). The reaction mixture was cooled to rt, poured onto saturated $NaHCO_3$ (50 mL), and was extracted with EtOAc (3×50 mL). The combined organic extracts were dried ($Na_2SO_4$), filtered, and concentrated to afford a brown solid. Purification by silica gel chromatography (hexanes/EtOAc, 3:1 with 2% $Et_3N$) afforded 200 mg (60%, 2 steps) of 17 as a light yellow crystalline solid. Data for 17: $^1$H NMR(400 MHz, benzene-$d_6$): 7.20 (dd, J=9.6, 2.8, 1H); 7.07 (d, J=8.6, 1H); 6.77 (dd, J=8.9, 4.6, 1H); 6.56 (td, J=8.4, 2.1, 1H); 6.38 (d, J=8.6, 1H); 5.24 (t, J=1.4, 1H); 4.79 (s, 1H); 3.50 (br s, 2H); 2.14 (s, 3H);

Step D 2,2-Diethyl-9-fluoro-1,2-dihydro-4-methyl-5-coumarino[3,4-f]quinoline (compound 20, structure 12, where $R^{1-2}=R^{4-6}=R^{17}=H$; $R^3$=fluoro; $R^{16}$=methyl; $R^{18-19}$=ethyl). In a 25-mL 2-neck flask was weighed out 17 (100 mg, 0.371 mmol) and camphorsulfonic acid (9 mg, 0.04 mmol, 10 mol %). The flask was evacuated, and the atmosphere replaced with nitrogen. Anhydrous toluene (8 mL) was added followed by 3-pentanone (0.056 mL, 0.56 mmol, 1.5 equiv). The suspension was heated to reflux for 1.5 h; the reaction mixture became homogeneous. $BF_3$-$Et_2O$ (0.005 mL, 0.04 mmol, 10 mol %) was added, and the reaction mixture was heated an additional 2.5 h. The reaction mixture was cooled to rt and poured onto saturated $NaHCO_3$ (50 mL). The aqueous layer was extracted with EtOAc (3×50 mL), and the combined organic extracts were washed with brine, dried ($Na_2SO_4$), filtered, and concentrated onto 20 mL Celite. Purification by silica gel chromatography (hexanes/$CH_2Cl_2$, 1:1 with 10% EtOAc) afforded 61 mg (50%) of 20 as a yellow solid. Data for 20: $^1$H NMR (400 MHz, acetone-$d_6$): 7.92 (d, J=8.6, 1H); 7.80 (dd, J=10.1, 2.9, 1H); 7.28 (dd, J=9.1, 4.9, 1H); 7.24 (d, J=8.9, 1H); 7.14 (td, J=8.5, 2.2, 1H); 6.12 (br s, 1H); 5.49 (br d, J=1.1, 1H); 2.10 (d, J=1.2, 3H); 1.61 (q, J=7.3, 4H); 0.91 (t, J=7.5, 3H);

Example 3

Step A

2-Amino-6-fluoro-1-(2-propenyl)-3,4-benzocoumarin (compound 17, structure 10 where $R^{1-2}=R^{4-6}=R^{17}$=H; $R^3$=fluoro; $R^{16}$=methyl). In an oven-dried 500-mL flask, a solution of 16 (1.075 g, 3.49 mmol) and N,O-bis(trimethylsilyl)acetamide (1.73 mL, 6.98 mmol, 2.0 equiv) in acetonitrile (200 mL) was treated with chlorotrimethylsilane (10 drops) and stirred 21 h at rt. The reaction mixture was concentrated to afford an orange solid, and was heated slightly in vacuo to remove any volatile material. The crude material was dissolved in DME (100 mL), tri(2-furyl)phosphine (162 mg, 0.698 mmol, 20 mol %) and 2-(tributylstannyl)propene (1.30 mL, 4.19 mmol, 1.2 equiv) were added, and the solution was degassed by freeze/pump/thaw three times. Tris(dibenzylideneacetone)dipalladium(0) (160 mg, 0.175 mmol, 0.05 eq) was added under positive $N_2$ pressure, and the reaction mixture was heated to reflux for 13 h. The cooled reaction mixture was poured into acetonitrile (100 mL), and the acetonitrile layer was washed with hexanes (3×100 mL). The hexane layer was extracted with acetonitrile (1×50 mL), and the combined acetonitrile extracts were filtered and concentrated. Purification by silica gel chromatography (hexanes:EtOAc, 3:1 with 2% TEA) afforded 450 mg (48%) of 17 as a yellow solid, identical to the material prepared previously.

Step B

9-Fluoro-1,2-dihydro-4-methyl-5-coumarino[3,4-f]quinoline-2-spiro-1'-cyclohexane (compound 21, structure 12, where $R^{1-2}=R^{4-6}=R^{17}$=H; $R^3$=fluoro; $R^{16}$=methyl; $R^{18-19}$=spiro-$(CH_2)_5$). In a 25 mL 2-neck flask was weighed out 17 (170 mg, 0.631 mmol). The flask was evacuated, and the atmosphere was replaced with nitrogen. Anhydrous toluene (8 mL) was added, followed by cyclohexanone (0.262 mL, 2.53 mmol, 4.0 eq) and $BF_3$-$Et_2O$ (0.008 mL, 0.06 mmol, 10 mol %). The reaction mixture was then heated to 80° C., and TLC indicated completion after 3.5 h. The reaction mixture was cooled to rt and poured onto saturated $NaHCO_3$ (50 mL). The aqueous layer was extracted with EtOAc (3×50 mL), and the combined organic extracts were washed with brine, dried ($Na_2SO_4$), filtered, and concentrated onto 20 mL Celite. Purification by silica gel chromatography (hexanes/$CH_2Cl_2$, 3:1 with 3% EtOAc) afforded 125 mg (57%) of 21 as a yellow solid. Data for 21: $^1$H NMR (400 MHz, acetone-$d_6$): 7.96 (d, J=8.6, 1H); 7.83 (dd, J=10.0, 2.9, 1H); 7.31 (d, J=8.6, 1H); 7.29 (dd, J=9.1, 4.6, 1H); 7.16 (td, J=8.5, 2.2, 1H); 6.24 (br s, 1H); 5.66 (br s, 1H); 2.08 (d, J=1.4, 3H); 1.82–1.35 (br m, 10H); $^{13}$C NMR (acetone-$d_6$): 160.2 (d, $J_{C-F}$=239), 160.0, 148.0, 147.3, 132.1, 131.3, 125.3 (d, $J_{C-F}$=2), 124.1, 123.0, 122.1, 121.8 (d, $J_{C-F}$=9), 119.1, 119.0 (d, $J_{C-F}$=9), 115.6 (d, $J_{C-F}$=25), 108.9 (d, $J_{C-F}$=25), 53.1, 37.4, 25.4, 22.3, 21.8.

Example 4

9-Fluoro-1,2-dihydro-2,4-dimethyl-2-phenyl-5-coumarino[3,4-f]quinoline (compound 22, structure 12, where $R^{1-2}=R^{4-6}=R^{17}$=H; $R^3$=fluoro; $R^{16}=R^{18}$=methyl; $R^{19}$=phenyl). In a 25-mL oven-dried 2-neck flask was weighed out 17 (106 mg, 0.394 mmol) and pyridinium p-toluenesulfonate (5 mg, 0.04 mmol, 0.1 eq). The flask was evacuated, and the atmosphere was replaced with nitrogen. Anhydrous toluene (8 mL) was added, followed by acetophenone (0.184 mL, 1.58 mmol, 4.0 eq). The suspension was heated to reflux for 45 min, and the reaction mixture became cloudy. $BF_3$-$Et_2O$ (0.005 mL, 0.04 mmol, 0.10 eq) was added under positive pressure of $N_2$, and the reaction mixture was heated an additional 1.5 h, until TLC indicated consumption of the starting material. The reaction mixture was cooled to rt and poured onto EtOAc (20 mL) and saturated $NaHCO_3$ (20 mL). The aqueous layer was extracted with EtOAc (3×10 mL), and the combined organic extracts were washed with brine (1×10 mL), dried ($Na_2SO_4$), filtered, and concentrated onto 20 mL Celite. Purification by silica gel chromatography (hexanes:$CH_2Cl_2$, 3:1 with 3% EtOAc) afforded 98 mg (67%) of 22 as a yellow solid. Data for 22: $^1$H NMR (400 MHz, acetone-$d_6$): 7.96 (d, J=8.7, 1H); 7.81 (dd, J=10.0, 2.8, 1H); 7.51 (d, J=7.8, 2H); 7.38 (d, J=8.6, 1H); 7.24 (m, 3H); 7.13 (m, 2H); 6.96 (br s, 1H); 5.91 (s, 1H); 2.16 (d, J=1.0, 3H); 1.70 (s, 3H); $^{13}$C NMR (acetone-$d_6$): 160.2 (d, $J_{C-F}$=239), 159.8, 149.3, 148.0, 147.4, 132.8, 131,8, 128.9, 127.4, 126.4, 125.8, 123.8, 123.2, 122.1, 121.6 (d, $J_{C-F}$=9), 119.1, 119.0 (d, $J_{C-F}$=9), 115.8 (d, $J_{C-F}$=24), 109.0 (d, $J_{C-F}$=25), 56.4, 30.9, 21.7.

Example 5

1.2-dihydro-4-methyl-2-spiro-1'-(4'-tert-butyl)-cyclohexane (compound 23, structure 15, where $R^{16}$=methyl, $R^{18-19}$=[$CH_2CH_2CH(t$-Bu$)CH_2CH_2$], $R^{17}=R^{20-23}$=H. In a 25-mL oven-dried 2-neck flask under $N_2$ was combined 2-isopropenylaniline (0.500 mL, 3.67 mmol), 4-tert-butylcyclohexanone (735 mg, 4.77 mmol, 1.3 eq), and anhydrous toluene (10 mL). The suspension was heated to reflux, and $BF_3Et_2O$ (0.046 mL, 0.04 mmol, 0.10 eq) was added under positive pressure of $N_2$. The reaction mixture was stirred at reflux 3 h, until TLC indicated consumption of the starting material. The reaction mixture was cooled to rt and poured onto EtOAc (40 mL) and saturated sodium bicarbonate (30 mL). The aqueous layer was extracted with EtOAc (3×10 mL), and the combined organic extracts were dried ($Na_2SO_4$), filtered, and concentrated. Purification by silica gel chromatography (hexanes: EtOAc, 80:1) afforded 813 mg (82%, 7:1 mixture of two diastereorners) of 23 as a colorless oil. Data for 23: $^1$H NMR (400 MHz, CDCl$_3$): (major isomer) 7.05 (d, J=7.4, 1H); 6.97 (td, J=7.6, 0.5, 1H); 6.64 (t, J=7.2, 1H); 6.51 (d, J=7.9, 1H); 5.19 (s, 1H); 4.26 (br s, 1H); 2.05 (d, J=11.6, 2H); 1.99 (d, J=1.0, 3H); 1.63 (d, J=12.7, 2H); 1.30–1.10 (m, 4H); 1.04–0.94 (m, 1H); 0.90 (s, 9H)

Example 6

1,2-dihydro-4-methyl-2,2-di-n-propylquinoline (compound 24, structure 15, where $R^{16}$=methyl, $R^{18-19}$=n-propyl, $R^{17}$=$R^{20-23}$=H). In a 25-mL oven-dried 2-neck flask under $N_2$ was combined 2-isopropenylaniline (0.500 mL, 3.67 mmol), 4-heptanone (0.667 mL, 4.77 mmol, 1.3 eq), and anhydrous toluene (10 mL). The suspension was heated to reflux, and $BF_3Et_2O$ (0.046 mL, 0.04 mmol, 0.10 eq) was added under positive pressure of $N_2$. The reaction mixture was stirred at reflux 16 h, until TLC indicated consumption of the starting material. The reaction mixture was cooled to rt and the solvent was removed by rotary evaporation. Purification by silica gel chromatography (hexanes:EtOAc, 80:1) afforded 566 mg (67%) of 24 as a colorless oil. Data for 24: $^1$H NMR (400 MHz, $CDCl_3$): 6.96 (dd, J=7.4, 1.0, 1H); 6.93 (td, J=7.6, 0.6, 1H); 6.53 (td, J=7.5, 0.4, 1H); 6.25 (d, J=7.9, 1H); 5.09 (s, 1H); 3.47 (br s, 1H); 1.98 (d, J=1.1, 3H); 1.46–1.30 (m, 8H); 0.88 (td, J=5.4, 1.0, 6H)

Example 7

1,2-dihydro-2,4-dimethyl-2-phenylquinoline (compound 25, structure 15, where $R^{16}$=$R^{18}$=methyl, $R^{19}$=phenyl, $R^{17}$=$R^{20-23}$=H). In a 25-mL oven-dried 2-neck flask under $N_2$ was combined 2-isopropenylaniline (0.500 mL, 3.67 mmol), acetophenone (0.860 mL, 7.34 mmol, 2.0 eq), and anhydrous toluene (10 mL). The suspension was heated to reflux, and $BF_3Et_2O$ (0.090 mL, 0.04 mmol, 0.20 eq) was added under positive pressure of $N_2$. The reaction mixture was stirred at reflux 3 h, until TLC indicated consumption of the starting material. The reaction mixture was cooled to rt and poured onto $Et_2O$ (40 mL) and saturated sodium bicarbonate (30 mL). The aqueous layer was extracted with $Et_2O$ (3×10 mL), and the combined organic extracts were washed with brine, dried ($Na_2SO_4$), filtered, and concentrated. Purification by silica gel chromatography (hexanes: $Et_2O$, 70:1) afforded 421 mg (49%) of 25 as a crystalline white solid. Data for 25: $^1$H NMR (400 MHz, acetone-$d_6$): 7.51 (d, J=7.2, 2H); 7.28 (t, J=7.7, 2H); 7.15 (t, J=7.3, 1H); 7.00 (d, J=7.5, 1H); 6.94 (td, J=7.6, 0.6, 1H); 6.72 (dd, J=7.9, 0.9, 1H); 6.51 (td, 7.3, 0.8, 1H); 5.64 (br s, 1H); 5.58 (s, 1H); 1.97 (d, J=1.46, 3H); 1.64 (s, 3H); $^{13}$CNMR (acetone-$d_6$): 151.1, 145.0, 129.5, 129.1, 128.9, 128.3, 127.1, 126.1, 124.4, 121.6, 117.1, 113.4, 57.5, 31.5, 18.8

We claim:

1. A process for the preparation of a 1,2-dihydroquinoline of structural formula 12,

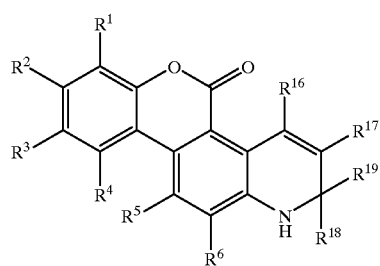

wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl or substituted aryl, heteroaryl or substituted heteroaryl), $NR^7R^9$, $SR^9$, $SOR^9$, or $SO_2R^9$;

$R^{16-17}$ independently represent H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; or where $R^{16}$ and $R^{17}$ taken together form a saturated or unsaturated five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered, optionally substituted ring;

that comprises the steps of:

a) treating a compound of structural formula 5

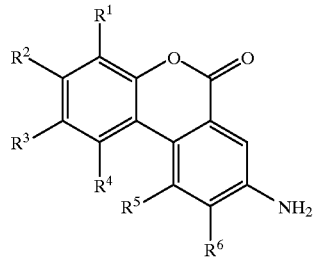

with a halogenating agent to form a compound of structural formula 8,

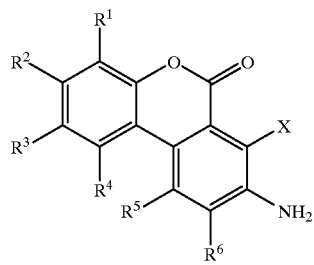

wherein X represents chloro, bromo, or iodo;

b) treating the ortho-haloaniline 8 with a metallated olefin in the presence of a catalyst or catalysts to form a compound of structural formula 10; and

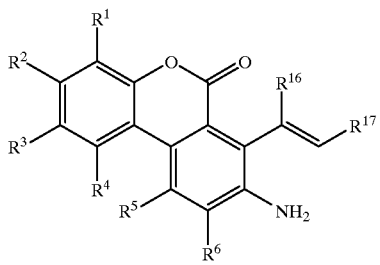

c) treating the ortho-alkenylaniline cross-coupling product 10 with a ketone in the presence of a catalyst to form a compound of structural formula 12.

2. The process of claim 1 wherein the halogenating agent of step (a) is a brominating agent or an iodinating agent.

3. The process of claim 1 wherein the metallated olefin of step (b) is an alkenyl borane or an alkenyl stannane.

4. The process of claim 1 wherein the catalyst or catalysts of step (b) are palladium catalysts.

5. The process of claim 1 wherein the ortho-alkenylaniline cross-coupling product 10 is either the E or Z isomer, or a mixture of both.

6. The process of claim 1 wherein the compound of structural formula 10 is treated with any ketone in the presence of a protic or Lewis acid to form the 1,2-dihydroquinoline 12.

7. A process for the preparation of a 1,2-dihydroquinoline of structural formula 12,

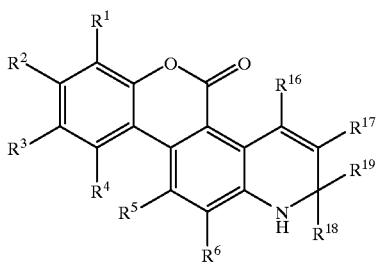

wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl or substituted aryl, heteroaryl or substituted heteroaryl), $NR^7R^9$, $SR^9$, $SOR^9$, or $SO_2R^9$;

$R^{16-17}$ independently represent H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; or where $R^{16}$ and $R^{17}$ taken together form a five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a saturated or unsaturated three- to eight-membered, optionally substituted ring;

that comprises the steps of:

a) treating a compound of structural formula 5

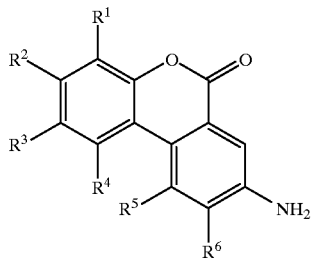

with a halogenating agent to form a compound of structural formula 8,

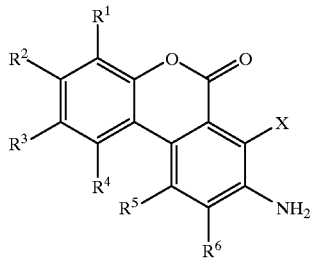

wherein X represents chloro, bromo, or iodo;

b) protecting the nitrogen of the ortho-haloaniline 8 derived to yield a compound of structural formula 13,

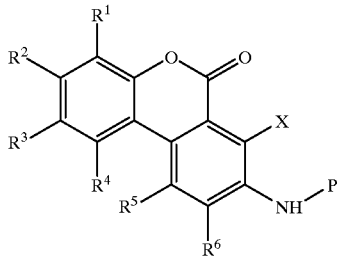

wherein P represents $SiR^{10}R^{11}R^{12}$ (where $R^{10-12}$ independently represent $C_1$–$C_6$ alkyl, substituted $C_1$–$C_6$ alkyl, allyl, substituted allyl, aryl, substituted aryl, heteroaryl or substituted heteroaryl); $COR^{13}$ (where $R^{13}$ represents $CF_3$, $C_1$–$C_6$ alkyl, substituted $C_1$–$C_6$ alkyl, aryl or substituted aryl); $CO_2R^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl); $CONR^{14}R^{15}$ (where $R^{15}$ represents H, $C_1$–$C_6$ alkyl, substituted $C_1$–$C_6$ alkyl, allyl, substituted allyl, aryl, substituted aryl, heteroaryl or substituted heteroaryl; or where $R^{14}$ and $R^{15}$ taken together form a five- to seven-membered ring); benzyl or substituted benzyl; or allyl or substituted allyl; and c) treating the N-protected ortho-haloaniline 13 with a metallated olefin in the presence of a catalyst or catalysts to yield an intermediate that is subsequently deprotected to form a compound of structural formula 10; and

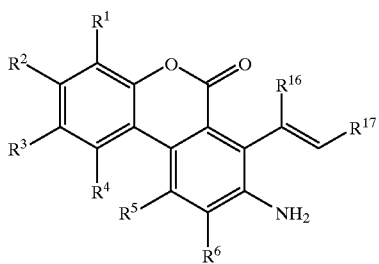

d) treating the ortho-alkenylaniline cross-coupling product 10 with a ketone in the presence of a catalyst to form a compound of structural formula 12.

8. The process of claim 7 wherein the halogenating agent of step (a) is a brominating agent or an iodinating agent.

9. The process of claim 7 wherein the nitrogen atom of the ortho-haloaniline is protected in step (b) as an N-trimethylsilyl analogue or as an N-trifluoroacetyl analogue.

10. The process of claim 7 wherein the metallated olefin of step (c) is an alkenyl borane or an alkenyl stannane.

11. The process of claim 7 wherein the catalyst or catalysts of step (c) are palladium catalysts.

12. The process of claim 7 wherein the ortho-alkenylaniline cross-coupling product 10 is either the E or Z isomer, or a mixture of both.

13. The process of claim 7 wherein the compound of structural formula 10 is treated with any ketone in the presence of a protic or Lewis acid to form the 1,2-dihydroquinoline 12.

14. A compound having the formula:

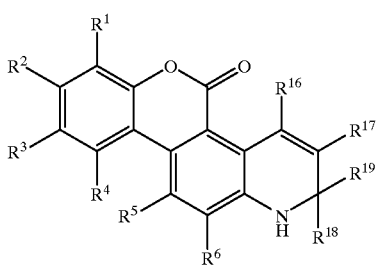

wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$;

$R^{16}$ represents H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; $R^{17}$ represents $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a saturated or unsaturated five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered, optionally substituted ring.

15. A compound of claim 14 wherein each of $R^{16, 18, 19}$ differs from the other two substitutents ($R^{16} \neq R^{18} \neq R^{19} \neq R^{16}$).

16. A compound of claim 14 wherein each of $R^{16-19}$ differs from the other three substituents ($R^{16} \neq R^{17} \neq R^{18} \neq R^{19}$; $R^{18} \neq R^{16} \neq R^{19} \neq R^{17}$).

17. A compound of claim 14 wherein $R^{16}$ and $R^{17}$ are identical ($R^{16}=R^{17}$).

18. A compound of claim 14 wherein $R^{17}$ and $R^{18}$ are identical ($R^{17}=R^{18}$).

19. A compound of claim 14 wherein $R^{17}$ and $R^{19}$ are identical ($R^{17}=R^{19}$).

20. A compound of claim 14 wherein $R^{18}$ and $R^{19}$ are identical ($R^{18}=R^{19}$), except that $R^{18}$ and $R^{19}$ cannot represent $CH_3$ ($R^{18, 19} \neq CH_3$).

21. A compound of claim 14 wherein $R^{16}$ and $R^{18}$ are identical ($R^{16}=R^{18}$), except that $R^{16}$, $R^{18}$ and $R^{19}$ cannot represent $CH_3$ ($R^{16, 18, 19} \neq CH_3$).

22. A compound of claim 14 wherein $R^{16}$ and $R^{19}$ are identical ($R^{16}=R^{19}$), except that $R^{16}$, $R^{18}$ and $R^{19}$ cannot represent $CH_3$ ($R^{16, 18, 19} \neq CH_3$).

23. A compound of claim 14 wherein $R^{16-18}$ are identical ($R^{16}=R^{17}=R^{18}$).

24. A compound of claim 14 wherein $R^{16, 17, 19}$ are identical ($R^{16}=R^{17}=R^{19}$).

25. A compound of claim 14 wherein $R^{17-19}$ are identical ($R^{17}=R^{18}=R^{19}$).

26. A compound of claim 14 wherein $R^{16, 18, 19}$ are identical ($R^{16}=R^{18}=R^{19}$), except that $R^{16, 18, 19}$ cannot represent $CH_3$ ($R^{16, 18, 19} \neq CH_3$).

27. A compound of claim 14 wherein $R^{16-19}$ are identical ($R^{16}=R^{17}=R^{18}=R^{19}$).

28. A compound of claim 14 that is a steroid receptor modulator.

29. A compound of claim 14 that is a progesterone receptor agonist.

30. A compound of claim 14 that is a progesterone receptor partial agonist.

31. A compound of claim 14 that is a progesterone receptor antagonist.

32. A method of affecting progesterone receptor activity comprising the in vivo administration of a compound of claim 14.

33. A method of modulating the activity of the progesterone receptor comprising administering to a patient an effective amount of a compound of claim 14.

34. A pharmaceutical composition comprising a therapeutically effective amount of the compound of claim 14, or the pharmaceutically acceptable salt thereof, and a pharmaceutically acceptable carrier.

35. A pharmaceutical composition of claim 34, wherein the composition is formulated for oral, topical, intravenous, suppository or parental administration.

36. A pharmaceutical composition of claim 34, wherein the compound is administered to a patient as a dosage unit from about 1 µg/kg of body weight to about 500 mg/kg of body weight.

37. A pharmaceutical composition of claim 34, wherein the compound is administered to a patient as a dosage unit from about 10 µg/kg of body weight to about 250 mg/kg of body weight.

38. A pharmaceutical composition of claim 34, wherein the compound is administered to a patient as a dosage unit from about 20 µg/kg of body weight to about 100 mg/kg of body weight.

39. A pharmaceutical composition of claim 34, wherein the composition is effective in: hormone replacement therapy; modulating fertility; pregnancy maintenance; treating dysfunctional uterine bleeding, dysmenorrhea, endometriosis, leiomyomas, and treating hormone dependent cancers such as cancers of the breast, ovaries, and endometrium.

40. A pharmaceutical composition that modulates progesterone receptor activity comprising an effective amount of a progesterone receptor modulating compound of the formula:

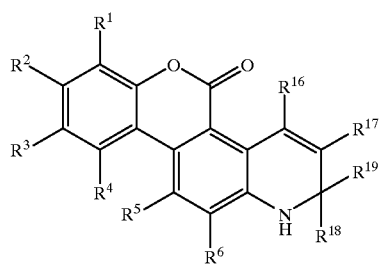

12 wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$;

$R^{16}$ represents H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; $R^{17}$ represents $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a saturated or unsaturated five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered, optionally substituted ring;

or the pharmaceutically acceptable salt thereof, and a pharmaceutically acceptable carrier.

41. A pharmaceutical composition of claim 40 comprising an agonistically effective amount of the progesterone receptor modulating compound.

42. A pharmaceutical composition of claim 40 comprising an partially agonistically effective amount of the progesterone receptor modulating compound.

43. A pharmaceutical composition of claim 40 comprising an antagonistically effective amount of the progesterone receptor modulating compound.

44. A pharmaceutical composition of claim 40, wherein the composition is formulated for oral, topical, intravenous, suppository or parental administration.

45. A pharmaceutical composition of claim 40, wherein the compound is administered to a patient as a dosage unit at from about 1 µg/kg of body weight to about 500 mg/kg of body weight.

46. A pharmaceutical composition of claim 40, wherein the compound is administered to a patient as a dosage unit at from about 10 µg/kg of body weight to about 250 mg/kg of body weight.

47. A pharmaceutical composition of claim 40, wherein the compound is administered to a patient as a dosage unit at from about 20 µg/kg of body weight to about 100 mg/kg of body weight.

48. A pharmaceutical composition of claim 40, wherein the composition is effective in: hormone replacement therapy; modulating fertility; pregnancy maintenance; treating dysfunctional uterine bleeding, dysmenorrhea, endometriosis, leiomyomas, and treating hormone dependent cancers such as cancers of the breast, ovaries, and endometrium.

49. A method of treating a patient requiring progesterone receptor therapy comprising administering to a patient an effective amount of a progesterone receptor modulating compound having the formula:

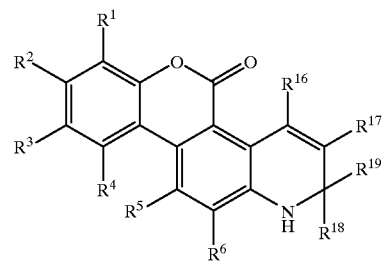

12 wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, or $SO_2R^9$;

$R^{16}$ represents H, $C_1$–$C_6$ alkyl, substituted $C_1$–$C_6$ alkyl, allyl, substituted allyl, aryl, substituted aryl, heteroaryl, substituted heteroaryl, $OR^{14}$ (where $R^{14}$ represents $C_1$–$C_6$ alkyl, substituted $C_1$–$C_6$ alkyl, allyl, substituted allyl, aryl, substituted aryl, heteroaryl or substituted heteroaryl) or Cl; $R^{17}$ represents $C_1$–$C_6$ alkyl, substituted $C_1$–$C_6$ alkyl, allyl, substituted allyl, aryl, substituted aryl, heteroaryl, substituted heteroaryl, $OR^{14}$ or Cl; or where $R^{16}$ and $R^{17}$ taken together form a saturated or unsaturated five- to seven-membered, optionally substituted ring;

and $R^{18-19}$ independently represent $C_1$–$C_6$ alkyl, substituted $C_1$–$C_6$ alkyl, allyl, substituted allyl, aryl, substituted aryl, heteroaryl or substituted heteroaryl; or where $R^{18}$ and $R^{19}$ taken together form a three- to eight-membered, optionally substituted ring.

50. A method of treating a patient according to claim 49, wherein the progesterone receptor modulating compound is a progestone receptor agonist.

51. A method of treating a patient according to claim 49, wherein the progesterone receptor modulating compound is a progestone receptor partial agonist.

52. A method of treating a patient according to claim 49, wherein the progesterone receptor modulating compound is a progestone receptor antagonist.

53. A method of treating a patient according to claim 49, wherein the progesterone receptor modulating compound is effective in: hormone replacement therapy; modulating fertility; pregnancy maintenance; treating dysfunctional uterine bleeding, dysmenorrhea, endometriosis, leiomyornas, and treating hormone dependent cancers such as cancers of the breast, ovaries, and endometrium.

* * * * *